United States Patent [19]

Schaefer

[11] Patent Number: 4,563,153

[45] Date of Patent: Jan. 7, 1986

[54] DENTAL COMPOSITION CONTAINING PIGMENT AND METHODS OF USING THE SAME

[75] Inventor: Roland Schaefer, Friedrichsdorf, Fed. Rep. of Germany

[73] Assignee: Kulzer & Co. GmbH, Wehrheim, Fed. Rep. of Germany

[21] Appl. No.: 556,025

[22] Filed: Nov. 29, 1983

[30] Foreign Application Priority Data

Dec. 7, 1982 [DE] Fed. Rep. of Germany ....... 3245172
Sep. 7, 1983 [DE] Fed. Rep. of Germany ....... 3332179

[51] Int. Cl.$^4$ .................. C08F 2/50; C08F 236/20; C08K 3/22
[52] U.S. Cl. .................. 433/223; 522/28; 522/81; 522/96
[58] Field of Search .................. 204/159.15, 159.18

[56] References Cited

U.S. PATENT DOCUMENTS

| | | | |
|---|---|---|---|
| 3,470,615 | 10/1969 | Petner | 264/19 |
| 4,054,683 | 10/1977 | Gruber | 204/159.23 |
| 4,071,424 | 1/1978 | Dart et al. | 204/159.15 |
| 4,257,915 | 3/1981 | Eaton | 204/159.23 |
| 4,269,869 | 5/1981 | Morahashi et al. | 204/159.14 |
| 4,327,014 | 4/1982 | Kawahara | 523/116 |
| 4,337,289 | 6/1982 | Reed | 204/159.16 |
| 4,411,625 | 10/1983 | Koblitz | 523/117 |
| 4,437,836 | 3/1984 | Schmitz | 204/159.18 |

*Primary Examiner*—John C. Bleutge
*Assistant Examiner*—A. H. Koeckert
*Attorney, Agent, or Firm*—Frishauf, Holtz, Goodman & Woodward

[57] ABSTRACT

A dental opaquing composition comprising (a) at least one polymerizable ester selected from esters of acrylic acid and methacrylic acid; (b) a photopolymerization catalyst; and (c) 30 to 90 percent by weight, based on the weight of said composition, of a pigment mixture consisting essentially of 50 to 66.6% by weight zirconium dioxide and 33.33 to 50% by weight of titanium dioxide. The present composition is useful in the making of metal-based crowns and bridges and to coat natural and false teeth.

20 Claims, No Drawings

DENTAL COMPOSITION CONTAINING PIGMENT AND METHODS OF USING THE SAME

The present invention relates to a dental opaquing composition containing at least one polymerizable ester including acrylic acid esters and methacrylic acid esters and a pigment. The dental composition is useful for opaquing a metal surface for crown and bridge prosthesis veneered with plastic material.

BACKGROUND OF THE INVENTION

In the manufacture of artificial dental crowns and bridges from plastic-faced metals, the metal framework is covered by a non-transparent, opaque material to keep the metal substrate from influencing the color of the plastic facing and to improve the bonding between the plastic facing and the metal. Such coatings are generally referred to in the art as opaque base masses.

U.S. Pat. No. 3,470,615 discloses a material adapted for this purpose which is produced from titanium dioxide, barium sulfate, aluminum oxide and polymer, dissolved in polyglycol dimethacrylate. The resulting resin is coated on the metal substrate and then hardened by heating for 2 to 20 minutes.

A synthetic resin mixture containing a copolymer of acrylonitrile and methyl methacrylate, pigment and an organic solvent (e.g. nitroparaffin and halogenated hydrocarbons) is disclosed in GB No. 1,418,004. The resin mixture provides an opaque layer on the substrate (e.g. metal crown) and is coated thereon by dissolving the copolymer in a solvent (e.g. nitromethane), dispersing the pigment in the solution, applying the solution to the substrate and permitting the organic solvent to evaporate. The pigments disclosed in the reference include silica, titanium dioxide, zinc oxide, iron oxide, barium sulfate, and mixtures thereof.

The prior art compositions are disadvantageous because they take a relatively long time to harden and/or require the use of organic solvents which must be removed after coating.

It is therefore an object of the present invention to provide a pigment-containing dental opaquing composition which does not require the use of organic solvents.

It is a further object of the present invention to provide a pigment-containing dental opaquing composition which rapidy hardens on a substrate such as a metal crown.

SUMMARY OF THE INVENTION

The present invention is directed to a dental opaquing composition which comprises at least one polymerizable ester including acrylic acid esters and methacrylic acid esters. The composition further includes a photopolymerization catalyst and a pigment comprising at least one compound selected from zirconium dioxide and tungsten trioxide.

The polymerizable esters which may be used in the present invention include all esters formed from acrylic acid and methacrylic acid by reaction of one of the abovementioned acids with a mono or polyhydroxyl compound and known in the dental field as components of dental resin material. Particularly preferred esters include the reaction product of methacrylic acid and a dihydroxy compound. Other preferred esters include urethane acrylates and urethane methacrylates and mixtures thereof. The urethane esters are reaction products of an organic diisocyanate and a hydroxyalkyl acrylate or methacrylate which are disclosed, for example, in U.S. Pat. No. 3,825,518 incorporated herein by reference.

The photopolymerization catalysts comprise a mixture of a photosensitizer and a reducing agent. The photosensitizer is preferably a ketone or a diketone and the reducing agent is preferably an amine as described in U.S. Pat. No. 4,071,424 incorporated herein by reference. The most preferred polymerization catalyst is camphor quinone as the photosensitizer and p-dimethylaminoethyl benzoate as the reducing agent.

The preferred amount of the pigment is in the range of from 30 to 90% by weight based on the total weight of the composition. The pigment may also include titanium dioxide which is present in an amount sufficient to replace up to 50% by weight of the amount of zirconium dioxide and/or tungsten trioxide.

The dental opaquing composition of the present invention is applied in a suitable manner (e.g. coating) to the metal substrate such as a metal crown to thereby form a layer. The layer is hardened by irradiation with visible light or with ultraviolet light. The resulting hardened layer provides excellent coverage of the metal substrate. The hardened layer provides sufficient coverage so that the metal is not visible and thus cannot influence the color of the plastic facing. The hardened layer binds tightly to the substrate and promotes adhesion between metal substrate and plastic facing.

The dental opaquing composition in accordance with the present invention which may include colored pigments is adapted not only for covering metal substrates for producing plastic-coated dental crowns and bridges, but may also be applied to other substrates such as natural teeth and false teeth originally composed of porcelain clad metal. The present composition therefore may be used to eliminate discolored natural teeth and to repair damaged false teeth.

The following examples are provided to illustrate embodiments of the invention and their behavior in polymerization when irradiated and not intended to limit the invention as set forth in the claims attended hereto.

Example 1

25% by weight of an aliphatic urethane dimethacrylate (sold under the trademark Plex 6661 manufactured by the Röhm Company, Darmstadt, Fed. Rep. Germany);
24% by weight of butandiol dimethacrylate;
1% by weight of camphor quinone;
0.5% by weight of p-dimethylaminoethyl benzoate; and
49.5% by weight of zirconium dioxide were mixed together. The mixture thus obtained was placed in a tube composed of Delrin ®, a polyacetal plastic, having an interior diameter of about 6 mm and a height of about 3 mm, and then irradiated for about 2 minutes by a tungsten-halogen lamp sold under the trademark TRANSLUX manufactured by Kulzer & Co. GmbH to form a polymerized material. Unpolymerized material was then removed. The resulting hardened layer had a thickness of 0.9 mm.

Example 2

25% by weight of an aliphatic urethane dimethacrylate (sold under the trademark Plex 6661 by the Röhm Company, Darmstadt, Fed. Rep. Germany);
24% by weight of butandiol dimethacrylate;
1% by weight of camphor quinone;

0.5% by weight of p-dimethylaminoethyl benzoate;
49.5% by weight of tungsten trioxide
were mixed together. The resulting mixture was treated in the same manner as Example 1 to provide a hardened layer having a thickness of 0.8% mm.

Example 3

12.2% by weight of an aliphatic urethane dimethacrylate (sold under the trademark Plex 6661 by the Röhm Company, Darmstadt, Fed. Rep. Germany);
11.5% by weight of butandiol dimethacrylate;
0.8% by weight of camphor quinone;
0.5% by weight of p-dimethylaminoethyl benzoate;
50% by weight of zirconium dioxide, and
25% by weight of titanium dioxide
were mixed together. The resulting mixture was treated in the same manner as Example 1 to provide a hardened layer having a thickness of 0.5 mm.

Example 4

24.5% by weight of an aliphatic urethane dimethacrylate (sold under the trademark Plex 6661 by the Röhm Company, Darmstadt Fed. Rep. Germany);
24% by weight of butandiol dimethacrylate;
1% by weight of camphor quinone;
0.5% by weight of p-dimethylaminoethyl benzoate;
25% by weight of zirconium dioxide, and
25% by weight of titanium dioxide
were mixed together. The resulting mixture was treated in the same manner as Example 1 to provide a hardened layer having a thickness of 0.4 mm.

Pigments used in the examples:
zirconium dioxide fine anhydrous powder supplied by Merck, Darmstadt
tungsten trioxide fine anhydrous powder supplied by Merck, Darmstadt
titanium dioxide Kronos ®C1 220 supplied by Kronos Titan-GmbH, Leverkusen As said before the preferred amount of the pigment is in the range of 30 to 90% by weight based on the total weight of the composition. The more preferred amount is in the range of about 45 to 75% by weight.

The photosensitizer is preferably present in an amount of 0,1% by weight to 5% by weight, most preferably from 0,5 to 2% by weight. The reducing agent is present preferably in an amount of 0,1 to 5% by weight, most preferably between 0,5 to 3% by weight.

The technique for producing a crown or bridge prosthesis veneered with a methacrylate resin crown and bridge material is first to paint one of the aforementioned paste-like dental opaquing compositions over the metal substrate of the crown or bridge prosthesis. When sufficient opaquing composition has been applied so as to mask the metal substrate, the layer of opaquing composition is then permitted to harden (to polymerize) by irradiation with visible light or with ultraviolet light, using for example the tungsten-halogen lamp sold under the trademark TRANSLUX manufactured by Kulzer & Co. GmbH. Then the methacrylate resin crown and bridge material is applied to the opaqued surface of the metal substrate to produce a plastic faced crown or bridge prosthesis in known manner.

What is claimed is:

1. A dental opaquing composition comprising
   (a) at least one polymerizable ester selected from esters of acrylic acid and methacrylic acid;
   (b) a photopolymerization catalyst; and
   (c) 30 to 90 percent by weight, based on the weight of said composition, of a pigment mixture consisting essentially of 50 to 66.67% by weight zirconium dioxide and 33.33 to 50% by weight titanium dioxide.
2. The dental composition of claim 1, wherein at least one of said polymerizable esters is the reaction product of one of said acids and a mono or polyhydroxy compound.
3. The dental composition of claim 1, wherein said pigment mixture is present in an amount of 45 to 75 percent by weight of said composition.
4. The dental composition of claim 3, wherein the ratio of zirconium dioxide to titanium dioxide is 2:1.
5. The dental composition of claim 3, wherein the ratio of zirconium dioxide to titanium dioxide is 1:1.
6. The dental composition of claim 5, wherein zirconium dioxide and titanium dioxide are each present in an amount of 25% by weight.
7. The dental composition of claim 1, wherein the photopolymerization catalyst comprises a ketone or diketone and an amine.
8. The dental composition of claim 7, wherein said diketone is camphor quinone.
9. The dental composition of claim 8, wherein said amine is p-dimethylaminoethyl benzoate.
10. The dental composition of claim 1, wherein said acrylate or a urethane ester is a urethane methacrylate.
11. The dental composition of claim 1, wherein said ester is an aliphatic urethane methacrylate ester.
12. The dental composition of claim 2, wherein said methacrylic acid ester is a urethane methacrylate.
13. A dental composition of claim 1 comprising an aliphatic urethane dimethacrylate, butandiol dimethacrylate, camphor quinone, and p-dimethylaminoethyl benzoate.
14. The dental composition of claim 13, wherein titanium dioxide and zirconium dioxide are each in an amount of 25% by weight.
15. The dental composition of claim 13, wherein zirconium dioxide is present in an amount of 50% by weight and titanium dioxide is present in an amount of 25% by weight.
16. A method of opaquing the metal substrate for crown and bridge prosthesis, comprising applying to the metal substrate the dental opaquing composition of Claim 1 and irradiating said substrate with visible or ultraviolet light.
17. The dental composition of claim 7, wherein said ketone or diketone is present in an amount of from 0.1 to 5% by weight and said amine is present in an amount of from 0.1 to 5% by weight.
18. The dental composition of claim 17, wherein said ketone or diketone is present in an amount of from 0.5 to 2% by weight and said amine is present in an amount of from 0.5 to 3% by weight.
19. The dental composition of claim 1, wherein the ratio of zirconium dioxide to titanium dioxide is 2:1.
20. The dental composition of claim 1, wherein the ratio of zirconium dioxide to titanium dioxide is 1:1.

* * * * *